United States Patent [19]

Ball et al.

[11] Patent Number: 4,533,649
[45] Date of Patent: Aug. 6, 1985

[54] METHOD OF PREPARING CRYSTALLINE ALUMINOSILICATES

[75] Inventors: William J. Ball, Capel; Sami A. I. Barri, London; Dennis Young, Staines, all of England

[73] Assignee: The British Petroleum Company p.l.c., London, England

[21] Appl. No.: 528,528

[22] Filed: Sep. 1, 1983

[30] Foreign Application Priority Data

Sep. 7, 1982 [GB] United Kingdom ............... 8225524

[51] Int. Cl.³ .................... C01B 33/28; B01J 29/28
[52] U.S. Cl. ................... 502/71; 423/328; 423/329; 502/77
[58] Field of Search .................. 423/326–333; 502/60, 71, 77

[56] References Cited

U.S. PATENT DOCUMENTS 4,452,907 6/1984 Ball et al. ........................ 502/60

FOREIGN PATENT DOCUMENTS 0036292 9/1981 European Pat. Off. .
0057049 8/1982 European Pat. Off. ............ 423/329

Primary Examiner—Edward J. Meros

Attorney, Agent, or Firm—Brooks Haidt Haffner & Delahunty

[57] ABSTRACT

The present invention relates to a process for producing crystalline aluminosilicates having in the hydrogen form an X-ray diffraction pattern substantially as set forth in Table 1 of this specification and the following composition in terms of the mole ratios of the oxides:

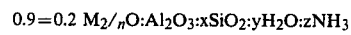

$$0.9 = 0.2\ M_{2/n}O:Al_2O_3:xSiO_2:yH_2O:zNH_3$$

wherein M is at least one cation having a valence n, x is at least 10, y/x is from 0 to 5 and z/x is 0–5. The process comprises mixing a source of silica, a source of alumina, a source of alkali metal(s), water and ammonia until a homogeneous gel is formed and crystallizing the gel at a temperature above 70° C. for a period of at least 2 hours. The crystalline aluminosilicate thus produced can be used, whether or not impregnated and/or ion-exchanged, as catalysts for any one of the following reactions: alkylation, dealkylation, dehydrocyclodimerization, aromatization, transalkylation, isomerization, dehydrogenation, hydrogenation, cracking, cyclization, oligomerization, polymerization, and dehydration reactions.

8 Claims, No Drawings

METHOD OF PREPARING CRYSTALLINE ALUMINOSILICATES

The present invention relates to an improved method of preparing crystalline aluminosilicates having catalytic properties, and hydrocarbon conversion therewith.

Zeolites are well known natural and synthetic compositions. Many of them have been demonstrated to have catalytic properties for various types of hydrocarbon and related reactions. Zeolites can be defined as ordered porous crystalline aluminosilicates having a framework structure sufficiently open to accommodate at least water molecules. Such structures generally contain a regular array of small voids interconnected by channels or pores. The dimensions of the voids and channels can range from those of water to those of quite large molecules. For a given framework structure, the dimensions of the voids and channels are limited to a small number of values, which can vary from structure to structure. Thus these structures are capable of absorbing molecules of certain dimensions while rejecting those of dimensions larger than a critical value which varies with structure. This had led to zeolites being used as molecular sieves. Zeolites belong to a class of materials that can be termed tectoaluminosilicates which comprises (in addition to zeolites) felspars and felspathoids. They can be defined as having a framework structure consisting of a rigid regular three dimensional network of $SiO_4$ and $AlO_4$ tetrahedra in which the tetrahedra are cross-linked by sharing the oxygen atoms. All oxygen atoms are shared, thus the ratio of total aluminium and silicon atoms to oxygen atoms is 1:2. The inclusion of aluminium in the framework leads to a net negative charge which is balanced by the inclusion in the crystal of an electrochemical equivalence of cations, for example alkali metal, alkaline earth metal, hydrogen or ammonium cations or mixtures thereof. This can be expressed by a formula in which the ratio of Al to the number of the various cations such as Ca/2, Sr/2, Na, K, Li or generally M/n (where n is the formal oxidation state of the cation) is equal to unity. Additionally in zeolites, but not in felspars and some felspathoids, the framework is sufficiently open to accommodate water molecules as well as cations. This enables these cations to be exchanged in their entirety or partially by other cations using ion-exchange techniques in a conventional manner. These materials can exhibit specific affinities for specific cations and can thus be used as selective ion-exchangers. By means of ion-exchange, it is possible to vary the size of the pores in a given crystalline zeolite material, modifying its molecular sieve properties. Also by means of ion-exchange the catalytic properties of these materials can be altered. In addition to the framework and charge-compensating cations, zeolites can contain other materials such as water and organic molecules, (hydrated) salts and oxides of eg Na, Al and Si introduced during synthesis, or formed or added during subsequent treatments. Zeolites are best characterised according to framework structure type, ie on the topology of the framework, irrespective of composition, distribution of different tetrahedral atoms, cell dimensions and symmetry. A code consisting of three capital letters has been adopted for each known structure type following the recommendations by IUPAC on zeolite nomenclature ("Chemical Nomenclature, and Formulation of Compositions, of Synthetic and Natural Zeolites," IUPAC yellow booklet, 1978) and a compilation of 38 known zeolite structure types has been published by The Structure Commission of the International Zeolite Association ("Atlas of Zeolite Structure Types", by Meier, W. M. and Olsen, D. H. (1978), distributed by Polycrystal Book Service, Pittsburgh, PA, USA). In addition to the groups classified by known structure type, there is a further group of crystalline zeolite materials whose X-ray diffraction patterns, sorption, ion-exchange and related properties indicate that they do not have known structure types but appear to have new, as yet undetermined structure types. An example of such a material is the novel porous crystalline aluminosilicate designated Theta-1 and described in our published co-pending European patent specification No. 0057049.

Our copending European application publication No. 0057049 describes a process for preparing the novel porous crystalline aluminosilicate, designated Theta-1, from a mixture containing a source of silica, a source of alumina, a source of alkali metal(s), water and an organic nitrogen-containing base, such as diethanolamine. Theta-1 has the following composition in terms of the mole ratios of the oxides:

$$0.9 \pm 0.2 M_{2/n}O : Al_2O_3 : xSiO_2 : yH_2O$$

wherein M is at least one cation having a valence n, x is at least 10 and y/x is between 0 to 25, wherein the aluminosilicate in the calcined hydrogen-form has an X-ray diffraction pattern substantially as set forth in Table A of that specification.

The aluminosilicate is preferably in the calcined hydrogen-form and has an X-ray diffraction pattern substantially as set forth in Table B that specification.

By the term "calcined hydrogen-form" is meant that the aluminosilicate is in a state wherein the majority of organics in the as-synthesized aluminosilicate have been removed by calcination and wherein the cation M is hydrogen.

It has now been found that the crystallinity and the surface area of the aluminosilicate designated Theta-1 can be substantially improved by using ammonia as the base during synthesis. Furthermore, the Theta-1 so produced does not require the relatively severe calcination to remove organics, and obviates the need to dispose of potentially hazardous materials such as organic nitrogen bases.

Accordingly, the present invention is a process for producing crystalline aluminosilicates having in the hydrogen form an X-ray diffraction pattern substantially as set forth in Table 1 of this specification and the following composition in terms of the mole ratios of the oxides:

$$0.9 \pm 0.2 M_{2/n}O : Al_2O_3 : xSiO_2 : yH_2O : zNH_3$$

wherein M is at least one cation having a valence n, x is at least 10 y/x is from 0 to 5 and z/x is 0–5, said process comprising mixing a source of silica, a source of alumina, a source of alkali metal(s), water and ammonia until a homogeneous gel is formed and crystallising the gel at a temperature above 70° C. for a period of at least 2 hours.

By the term "hydrogen form" is meant that the aluminosilicate prepared from ammonia is in a state wherein the cation M is hydrogen. This state when applied to aluminosilicates prepared from ammonia, is also free of organic materials. Thus it is equivalent to the "calcined hydrogen form" of aluminosilicates prepared from organic nitrogencontaining bases.

The cation M in the zeolite may be selected from H+, ammonium, alkali metal cations, alkaline earth metal cations, aluminium cations, gallium cation and mixtures thereof.

The cations present in the aluminosilicate may be replaced using conventional ion exchange techniques either wholly or partially by other cations e.g. hydrogen ions, ammonium ions or metal cations.

The hydrogen-form of the aluminosilicate zeolite may be produced by known methods such as exchange with hydrogen ions or with ammonium cations followed by one or more calcination steps, or a combination of the two including one or more calcination stages if ammonium ions are still present after the exchange steps.

The $H_2O$ content "y" of the aluminosilicate is the water of hydration and will depend, within the ratios set out above, upon the conditions under which it is dried, calcined, subjected to further aqueous treatments or combinations thereof after synthesis. The $H_2O$ content "y" does not include water notionally present when the cation M represents hydrogen.

The content "z" of ammonia in the aluminosilicate will also depend upon the conditions under which it is washed, calcined or subjected to further aqueous treatments or combinations thereof after synthesis, and also on the synthesis parameters of the aluminosilicate, particularly the proportion of ammonia present in the original hydrogel.

The aluminosilicates according to the present invention, designated herein as "Theta-1" aluminosilicates, have in the hydrogen form an X-ray diffraction pattern shown in Table 1 below.

The specific values in the Tables were determined using copper K-alpha radiation and a computer step scan.

The peak heights, I, and their position as a function of 2 theta, where theta is the Bragg angle, were read from the spectrometer output. From this output the relative intensities $100 \times I/I_o$, where $I_o$ is the intensity of the strongest peak and d the interplanar spacing in Å, corresponding to the recorded peaks were calculated.

It will be understood by those skilled in the art that the X-ray diffraction pattern of aluminosilicates may vary in the values of $I/I_o$ and the d-spacing depending for example upon whether the sample being examined is calcined or uncalcined, upon the temperature of calcination, upon the nature of the cation present in the aluminosilicate, the mole ratio of silica to alumina, and the particle size of the aluminosilicate.

The aluminosilicate is produced from an initial mixture containing a source of silica, a source of alumina, a source of alkali metal(s), water and ammonia.

The silica to alumina mole ratio in the initial mixture may suitably be at least 10:1. Preferably the silica to alumina mole ratio is greater than 40:1 and the free alkali metal(s) hydroxide to water mole ratio, defined as:

$$\frac{[(\text{Number of moles of total alkali metal(s)}) - (\text{Number of moles of alkali metal(s) required to convert alumina present to alkali metal aluminate(s), ie MAlO}_2)]}{\text{Number of moles of water present}}$$

is suitably greater than $2 \times 10^{-3}$:1. Even more preferably the silica to alumina mole ratio is in the range 60:1 to 500:1 and the free alkali metal(s) hydroxide to water mole ratio is in the range $2 \times 10^{-3}$:1 to $8 \times 10^{-1}$:1. Similarly the mole ratio of free alkali metal(s) hydroxide to silica may suitably be below 5:1, preferably from 0.01:1 to 1:1, most preferably from 0.02:1 to 0.5:1. The mole ratio of water to silica may suitably be in the range 0 to 100:1, preferably in the range 5:1 to 50:1, even more preferably in the range 7:1 to 20:1. In the initial mixture the mole ratio of ammonia to silica is suitably from 0.01:1 to 25:1, preferably from 0.2:1 to 10:1 and most preferably from 0.5:1 to 4:1.

Using ammonia as the base, Theta-1 substantially free from other crystalline aluminosilicates, eg MFI-type zeolite (as defined in the "Atlas of Zeolite Structure Types" by Meier and Olsen referred to above), can be produced at a silica to alumina mole ratio of from 45 to 150:1, and an ammonia to silica molar ratio of from 0.5:1 to 4:1 in the initial mixture.

The aluminosilicate, Theta-1, is suitably prepared by forming a mixture of all the reactants, by simply mixing them together while maintaining the mixture suitably at a temperature from 0° to 100° C., preferably from 20° to 60° C., until a homogeneous gel is formed and crystallising the gel so-formed at a temperature above 70° C., preferably from 100° to 220° C. for a period of at least 2 hours, preferably for 6 to 240 hours. The optimum crystallisation period can vary and may depend upon such factors as the temperature, pH, agitation and gel composition. Suitable sources of silica include, for example, sodium silicate, silica hydrosol, silica gel, silica sol and silicic acid. The preferred source of silica is an aqueous colloidal dispersion of silica particles. It is preferred that the silica source is added to the other reagents in such a way as to commence gelation at a relatively high pH.

The product obtained in this manner contains cations which may be hydrogen, alkali metal(s), aluminium, or ammonium or any combination thereof.

The cations in the product may be converted to hydrogen to give rise to the hydrogen-form of the product. This may be achieved by techniques known to those skilled in the art, e.g. (a) ammonia exchange followed by calcination, (b) acid exchange or a combination of (a) and (b).

The product or the hydrogen-form thereof may also be subjected to ion-exchange or impregnation with a metal suitable for imparting a specific type of catalytic activity. The metal compounds which may be used for ion-exchange and/or impregnation may be compounds of any one of the following metals or groups of metals, namely those belonging to Groups IB, IIB, IIIA, IVA, VA, VIIB and VIII according to the Periodic Table due to Mendeleef. Specifically, compounds of copper, silver, zinc, aluminium, gallium, indium, thallium, lead, antimony, bismuth, chromium, molybdenum, tungsten, manganese, iron, cobalt, nickel, ruthenium, rhodium, palladium, iridium, platinum, rhenium, thorium and the rare earths are preferred.

TABLE 1

| 2 theta | d-spacing | Relative intensity $100 \times I/I_o$ |
|---|---|---|
| 8.15 ± 0.2 | 11.1–10.6 | 60 to 100 |
| 10.16 ± 0.2 | 8.88–8.54 | 10 to 30 |
| 12.77 ± 0.2 | 7.04–6.83 | 10 to 30 |
| 16.36 ± 0.2 | 5.48–5.35 | 5 to 15 |
| 19.42 ± 0.2 | 4.62–4.52 | 5 to 15 |
| 20.35 ± 0.2 | 4.41–4.32 | 60 to 100 |
| 24.22 ± 0.2 | 3.70–3.65 | 60 to 90 |

TABLE 1-continued

| 2 theta | d-spacing | Relative intensity 100 × I/I$_o$ |
|---|---|---|
| 24.65 ± 0.2 | 3.64–3.58 | 40 to 70 |
| 25.75 ± 0.2 | 3.49–3.43 | 25 to 55 |
| 35.63 ± 0.2 | 2.53–2.51 | 5 to 15 | scanned up to 2 theta = 36

The aluminosilicate products of the present invention may be bound in a suitable binding material before or after impregnation or before or after exchange with one of the aforementioned metal compounds to produce an attrition resistant catalyst. The binder for this purpose may be any one of the conventional alumina or silica binders.

The aluminosilicates of the present invention may be used, whether or not impregnated and/or ion-exchanged, as catalysts for any of the following reactions: alkylation, dealkylation, dehydrocyclodimerisation, aromatisation, transalkylation, isomerisation, dehydrogenation, hydrogenation, cracking, cyclisation, oligomerisation, polymerisation, and dehydration reactions, particularly dehydration of alcohols and ethers. The aluminosilicate Theta-1 may be used as such or as a component of a catalyst mixture containing other active or inactive components. The Theta-1 may be used in admixture with other zeolites. The catalysts may be used in the form of fixed, fluidised or moving beds.

The present invention is further illustrated with reference to the following Examples.

EXAMPLE 1

A solution was prepared from a mixture of sodium aluminate (9.1 g), sodium hydroxide (5.5 g) and water (84 g).

Aqueous ammonia solution (494 g containing 25% by weight ammonia) was added to the solution and the resultant solution ("A") was stirred at room temperature for 5 minutes.

422 g of a commercial silica gel, "Ludox AS40" (Reg. Trade Mark) which contains 40% by weight of silica was added to solution "A" over a period of 10 minutes with vigorous stirring. Stirring was continued for a further 20 minutes. The resultant gel, which had the following composition $2.96Na_2O:100(NH_4)_2O:Al_2O_3:77SiO_2:975H_2O$, was transferred to a stainless steel pressure vessel and crystallised with agitation at 170° C. for 48 hours.

The product was filtered, washed and dried at 90° C. It was found by X-ray diffraction to be very crystalline Theta-1 zeolite and had a pattern as shown in Table 2 below. The zeolite product was shown to contain Si (40.4% w/w), Al (1.45% w/w) and Na (0.53% w/w).

EXAMPLE 2

A solution was prepared from a mixture of sodium aluminate (9.1 g), and sodium hydroxide (5.5 g) in water (120 g).

Aqueous ammonia solution (702 g containing 25% w/w ammonia) was added to the solution and the resultant solution "B" was stirred for 5 minutes at room temperature.

600 g of a commercial silica gel Ludox AS 40 (Regd. Trade Mark), which contains 40% by weight of silica was added to solution B, over 10 minutes with vigorous stirring and stirring was continued for a further 20 minutes. The resultant gel of composition $2.70Na_2O:8.5(NH_4)_2O:Al_2O_3:66.3SiO_2:842H_2O$ was transferred to a stainless steel pressure vessel and crystallised with agitation at 170° C. for 48 hours. The product was filtered, washed and dried at 90° C. It was found by X-ray diffraction, to be very good crystalline Theta-1. The product contained Si (37.5% w/w), Al (1.10% w/w) and Na (0.85% w/w).

EXAMPLE 3

A solution was prepared from a mixture of sodium aluminate (2.1 g), sodium hydroxide (0.67 g) and water (10 g). Aqueous ammonia solution (59 g containing 25% by weight ammonia) was added and the resultant solution "C" was stirred at room temperature for 5 minutes. 50 g of a commercial silica gel "Ludox AS40" (Reg. Trade Mark) which contains 40% by weight of silica, was added to solution C over a period of 10 minutes with vigorous stirring which was continued for a further 20 minutes. The resultant gel of composition $2.32Na_2O:64(NH_4)_2O:Al_2O_3:49.4SiO_2:629H_2O$ was transferred to a stainless steel pressure vessel and crystallised with agitation at 170° C. for 48 hours. The product was filtered, washed and dried at 90° C. It was found by X-ray diffraction to be a good crystalline Theta-1 product with a trace of MFI zeolite. The product was filtered, washed and dried at 90° C. The product was shown to contain Si(37.0%), Al(1.45%) and Na(0.53%).

COMPARATIVE TEST 1

A solution was prepared from a mixture of sodium aluminate (12.6 g), sodium hydroxide (6.65 g) and water (140 g). Diethanolamine (DEA) (180 g) was melted and added to the solution and the resultant solution "D" was stirred and maintained at 30° C. for 10 minutes with constant stirring. 500 g of commercial silica gel, Ludox AS40 (Reg. Trade Mark) which contains 40% by weight of silica, was diluted with 354 g of water to form solution "E". Thereafter solution E was added dropwise to solution D over a period of 40 minutes with constant stirring which was continued for further 20 minutes. The resultant gel of composition $2.8Na_2O:3.5DEA:Al_2O_3:68SiO_2:893H_2O$, was crystallised at 175° C. for 18 hours. The crystals were washed and dried and the product was found by X-ray powder diffraction to the good crystalline Theta-1.

COMPARATIVE TEST 2

The procedure of Comparative Test 1 above was followed except that 1.4 g of sodium aluminate was used instead of 12.6 g. The gel of composition $2.6Na_2O:31DEA:Al_2O_3:61SiO_2:803H_2O$ was crystallised at 175° C. for 24 hours. The crystals were washed and dried and the product was found by X-ray powder diffraction to be good crystalline Theta-1.

Table 3 compares the half peak height widths of the powder X-ray diffraction patterns of the hydrogen forms of Example 2 and Comparative Test 1 taken under identical conditions. As can be seen, those of Test 1 are usually wider, indicating a lower crystallinity.

Table 4 compares the height of the background lines associated with amorphous material in the powder X-ray diffraction patterns of the hydrogen forms of Examples 1 and 2 and Comparative Tests 1 and 2 taken under identical conditions. Those of Tests 1 and 2 are usually higher indicating a greater contribution from amorphous material.

Table 4 also compares the total integrated areas of the powder X-ray diffraction patterns of the hydrogen forms of Examples 1 and 2 and Comparative Tests 1 and 2 taken under identical conditions. Those of Examples 1 and 2 are higher indicating a greater crystallinity.

For the purposes of comparison, the crystalline aluminosilicate products of Examples 1 and 2 and Comparative Tests 1 and 2 were converted to their hydrogen forms in identical manners. This consisted of calcining at 590° C. for 60 hours, exchanging with solutions of acid and ammonium ions, and calcining for 16 hours at 590° C. Note that the first calcination, for the purpose of removing organics, is essential only for Tests 1 and 2, but was included in the cases of Examples 1 and 2 to achieve identical treatment procedures and thus stricter comparisons.

TABLE 2

| 2 theta | d-spacing | Relative Intensity 100 × I/Io |
|---|---|---|
| 8.08 | 10.95 | 100 |
| 10.07 | 8.78 | 21 |
| 12.72 | 6.96 | 23 |
| 16.30 | 5.44 | 11 |
| 19.36 | 4.59 | 11 |
| 20.29 | 4.38 | 90 |
| 24.16 | 3.68 | 76 |
| 24.56 | 3.62 | 52 |
| 25.66 | 3.47 | 35 |

Scanned up to 2 theta = 32
Peaks below I/Io = 5 were not included

Table 5 compares the specific surface areas (as determined by the standard $N_2$ adsorption BET method) of the hydrogen forms of Examples 1 and 2 and Comparative Test 1. Those of Examples 1 and 2 are much higher than those of Test 1.

TABLE 3

| d spacing (approx) | 2 theta (approx) | Width at half peak height (arbitrary units) | |
|---|---|---|---|
| | | Example 2 | Test 1 |
| 10.8 | 8.2 | 0.33 | 0.35 |
| 8.7 | 10.2 | 0.35 | 0.37 |
| 6.9 | 12.8 | 0.33 | 0.39 |
| 5.4 | 16.4 | 0.36 | 0.36 |
| 4.6 | 19.4 | 0.29 | 0.38 |
| 4.4 | 20.4 | 0.31 | 0.33 |
| 3.67 | 24.2 | 0.55 | 0.77 |
| 3.61 | 24.7 | 0.87 | 0.89 |
| 3.46 | 25.8 | 0.36 | 0.42 |

TABLE 4

| XRD Parameters | Example 1 | Example 2 | Test 1 | Test 2 |
|---|---|---|---|---|
| Relative Total Area (1) | 1.15 | 1.00 | 0.80 | 0.95 |
| Relative Base Line Heights (2) | | | | |
| at 2 theta = 22.5 | 0.75 | 1.00 | 2.13 | 1.75 |
| at 2 theta = 4.0 | 1.11 | 1.00 | 1.11 | 1.78 |

(1) Total integrated area between 2-theta values 4.0 to 32.0 inclusive, relative to that of Example 2.
(2) Difference between background baseline associated with amorphous material and zero intensity, relative to Example 2.

TABLE 5

| | Example 1 | Example 2 | Test 1 |
|---|---|---|---|
| BET Surface Area ($M^2/g$) | 114 | 114 | 78 |

We claim:
1. A process for producing crystalline aluminosilicates having in the hydrogen form an X-ray diffraction pattern substantially as set forth in Table 1 of this specification and the following composition in terms of the mole ratios of the oxides:

$$0.9 \pm 0.2 M_{2/n}O:Al_2O_3:xSiO_2:yH_2O:zNH_3$$

wherein M is at least one cation having a valence n, x is at least 10, y/x is from 0 to 5 and z/x is 0–5,
said process comprising mixing a source silica, a source of alumina, a source of alkali metal (s), water and ammonia,
wherein the silica to alumina mole ratio in the initial mixture is from 45 to 150:1,.
wherein the free alkali metal (s) hydroxide to water mole ratio is from $2 \times 10^{-3}:1$ to $8 \times 10^{-3}:1$,
wherein the free alkalii metal (s) hydroxide to silica mole ratio is 0.01:1 to 1:1,
wherein the water to silica mole ratio is from 5:1 to 50:1, and
wherein the ammonia to silica mole ratio is from 0.5:1 to 4:1,
until a homogeneous gel is formed and crystallising the gel at a temperature above 70° C. for a period of at least 2 hours.

2. A process according to claim 1 wherein the cations present in the aluminosilicate are replaced either wholly or partially by other cations comprising ammonium ions or metal cations.

3. A process according to claim 1 wherein the product is subjected to ion-exchange or impregnation with any one of the metals or groups of metals or their compounds selected from Groups IB, IIB, IIIA, IVA, VA, VIB, VIIB and VIII according to the Periodic Table due to Mendeleef.

4. A process according to claim 1, wherein the crystalline aluminosilicate product, is subjected to ion-exchange or impregnation with a metal suitable for imparting a specific type of catalytic activity.

5. A process according to claim 4 wherein the aluminosilicate is bound in a binding material before or after impregnation, or, before or after ion-exchange with one of the metal compounds to produce an attrition resistant catalyst.

6. A process according to claim 1 wherein the cations present in the aluminosilicate are replaced either wholly or partially by hydrogen ions.

7. A process according to claim 6, wherein the hydrogen form of the crystalline aluminosilicate product is subjected to ion-exchange or impregnation with a metal suitable for imparting a specific type of catalytic activity.

8. A process according to claim 6 wherein the hydrogen-form of the product is subjected to ion-exchange or impregnation with any one of the metals or groups of metals or their compounds selected from Groups IB, IIB, IIIA, IVA, VA, VIB, VIIB and VIII according to the Periodic Table due to Mendeleef.

* * * * *

UNITED STATES PATENT AND TRADEMARK OFFICE
CERTIFICATE OF CORRECTION

PATENT NO. : 4,533,649

DATED : August 6, 1985

INVENTOR(S) : WILLIAM J. BALL et al

It is certified that error appears in the above-identified patent and that said Letters Patent is hereby corrected as shown below:

In the Formula contained in the Abstract, "0.9=0.2" should read --0.9+0.2--

Col. 4, line 1, "$8 \times 10^{-1}:1$" should read --$8 \times 10^{-3}:1$--

Col. 4, line 52, after "VA," --VIB-- is omitted.

Signed and Sealed this

Twelfth Day of November 1985

[SEAL]

Attest:

DONALD J. QUIGG

Attesting Officer

Commissioner of Patents and Trademarks